(12) United States Patent
Di Pietro

(10) Patent No.: US 9,370,553 B2
(45) Date of Patent: Jun. 21, 2016

(54) METHODS FOR WEIGHT LOSS AND KETOGENIC COMPOSITIONS

(71) Applicant: EUROPEAN KETOGENIC WEIGHT LOSS CLINICS LLC, Bay Harbor Islands, FL (US)

(72) Inventor: Oliver R. Di Pietro, Bay Harbor Islands, FL (US)

(73) Assignee: EUROPEAN KETOGENIC WEIGHT LOSS CLINIC LLC, Bay Harbor Islands, FL (US)

( * ) Notice: Subject to any disclaimer, the term of this patent is extended or adjusted under 35 U.S.C. 154(b) by 75 days.

(21) Appl. No.: 14/543,624

(22) Filed: Nov. 17, 2014

(65) Prior Publication Data

US 2015/0072925 A1    Mar. 12, 2015

Related U.S. Application Data

(60) Division of application No. 13/589,820, filed on Aug. 20, 2012, now Pat. No. 8,940,689, which is a continuation-in-part of application No. 13/466,372, filed on May 8, 2012, now abandoned, which is a continuation of application No. PCT/US2012/051448, filed on Aug. 17, 2012.

(60) Provisional application No. 61/525,581, filed on Aug. 19, 2011.

(51) Int. Cl.

| | |
|---|---|
| A61K 38/16 | (2006.01) |
| A61K 38/17 | (2006.01) |
| A23L 1/30 | (2006.01) |
| A23L 1/302 | (2006.01) |
| A23L 1/304 | (2006.01) |
| A23L 1/305 | (2006.01) |
| A23L 1/29 | (2006.01) |
| A61K 31/191 | (2006.01) |
| A61K 31/202 | (2006.01) |
| A61K 31/341 | (2006.01) |
| A61K 31/355 | (2006.01) |
| A61K 31/4188 | (2006.01) |
| A61K 31/4406 | (2006.01) |
| A61K 31/4415 | (2006.01) |
| A61K 31/51 | (2006.01) |
| A61K 31/519 | (2006.01) |
| A61K 31/525 | (2006.01) |
| A61K 31/59 | (2006.01) |
| A61K 31/714 | (2006.01) |
| A61K 33/00 | (2006.01) |
| A61K 33/06 | (2006.01) |
| A61K 33/42 | (2006.01) |
| A61K 45/06 | (2006.01) |
| A61K 38/01 | (2006.01) |

(52) U.S. Cl.
CPC ............. *A61K 38/1709* (2013.01); *A23L 1/293* (2013.01); *A23L 1/296* (2013.01); *A23L 1/302* (2013.01); *A23L 1/304* (2013.01); *A23L 1/3006* (2013.01); *A23L 1/3051* (2013.01); *A61K 31/191* (2013.01); *A61K 31/202* (2013.01); *A61K 31/341* (2013.01); *A61K 31/355* (2013.01); *A61K 31/4188* (2013.01); *A61K 31/4406* (2013.01); *A61K 31/4415* (2013.01); *A61K 31/51* (2013.01); *A61K 31/519* (2013.01); *A61K 31/525* (2013.01); *A61K 31/59* (2013.01); *A61K 31/714* (2013.01); *A61K 33/00* (2013.01); *A61K 33/06* (2013.01); *A61K 33/42* (2013.01); *A61K 38/011* (2013.01); *A61K 38/012* (2013.01); *A61K 38/018* (2013.01); *A61K 45/06* (2013.01); *A23V 2002/00* (2013.01)

(58) Field of Classification Search
CPC .................................................. A61K 38/1709
See application file for complete search history.

(56) References Cited

U.S. PATENT DOCUMENTS

| | | | |
|---|---|---|---|
| 5,308,832 | A | 5/1994 | Garleb et al. |
| 7,744,930 | B2 | 6/2010 | Fisher et al. |
| 2002/0160081 | A1 | 10/2002 | Tiano et al. |
| 2005/0019372 | A1 | 1/2005 | Corkey et al. |
| 2006/0076025 | A1 | 4/2006 | Kim |
| 2006/0105938 | A1 | 5/2006 | Siemensma et al. |
| 2010/0179104 | A1 | 7/2010 | Wassenaar |

FOREIGN PATENT DOCUMENTS

WO     2006047051 A2     5/2006

OTHER PUBLICATIONS

Freedland et al., "Carbohydrate Restriction, Prostate Cancer Growth, and the Insulin-Like Growth Factor Axis," The Prostate, vol. 68, pp. 11-19 (2008).

Han et al., "Effects of Dietary Medium-Chain Triglyceride on Weight Loss and Insulin Sensitivity in a Group of Moderately Overweight Free-Living Type 2 Diabetic Chinese Subjects," Metabolism Clinical and Experimental, vol. 56, pp. 985-991 (2007).

Johnstone et al., "Effects of a High-Protein Cacogenic Diet on Hunger, Appetite, and Weight Loss in Obese Men Feeding Ad Libitum," Am J Clin Nutr., vol. 87, pp. 44-55 (2008).

(Continued)

*Primary Examiner* — Amber D Steele
(74) *Attorney, Agent, or Firm* — McDermott Will & Emery LLP

(57) ABSTRACT

The present disclosure relates to a weight-loss composition including protein and fat and methods of use. The weight loss composition is substantially free of carbohydrates. The composition induces body weight loss when administered to a subject as the only source of nutrition for at least 12 hours.

10 Claims, No Drawings

(56) References Cited

OTHER PUBLICATIONS

G. Cappello and A. Cappello, Abstract of "Ketogenic Enteral Nutrition (KEN) in the Treatment of Obesity: Short-Term and Long-Term Results of 19,000 Patients," University of Rome La Sapienz (Department of Surgery), Rome, Italy.

International Search Report w/Written Opinion issued in International Application No. PCT/US2012/051448 dated Feb. 28, 2013.

St-Onge, "Medium-versus long-chain triglycerides for 27 days increase fat oxidation and energy expenditure without resulting in changes in body composition in overweight women", International Journal of Obesity, 27-95-102, 2003.

U.S. Office Action issued in U.S. Appl. No. 13/589,820, dated Feb. 4, 2013.

U.S. final Office Action issued in U.S. Appl. No. 13/589,820, dated Jul. 1, 2013.

U.S. Office Action issued in U.S. Appl. No. 13/589,820, dated May 28, 2014.

U.S. Notice of Allowance issued in U.S. Appl. No. 13/589,820, dated Oct. 28, 2014.

Extended European Search Report dated Feb. 20, 2015 issued in European Patent Application No. 12825537.9.

Bach, et al., "Metabolic Effects of Medium- or Long-Chain Triglycerides and High-Protein, Carbohydrate-Free Diets in Zucker Rats," Metabolism, Clinical and Experimental, W. B. Saunders Co., Philadelphia, PA, vol. 33, No. 10, Oct. 1, 1984, pp. 951-958.

Klepper, et al., "Introduction of a Ketogenic Diet in Young Infants," Journal of Inherited Metabolic Disease, vol. 25, No. 6, Nov. 1, 2002, pp. 449-460.

Veldhorst, et al., "Presence or Absence of Carbohydrates and the Proportion of Fat in a High-Protein Diet Affect Appetite Suppression But Not Energy Expenditure in Normal-Weight Human Subjects Fed in Energy Balance," British Journal of Nutrition, vol. 104, 2010, pp. 1395-1405.

Yamaoka, et al., "Circadian Changes in Core Body Temperature, Metabolic Rate and Locomotor Activity in Rats on a High-Protein, Carbohydrate-Free Diet," J. Nutr. Sci. Vitaminol., Vol. 55, 2009, pp. 511-517.

Colombian Office Action dated Mar. 27, 2015, issued in corresponding Colombian Patent Application No. 14-031.972, (with English translation), 15 pgs.

METHODS FOR WEIGHT LOSS AND KETOGENIC COMPOSITIONS

RELATED APPLICATIONS

This Application is a Divisional of U.S. application Ser. No. 13/589,820, filed on Aug. 20, 2012, which is a continuation-in-part application of U.S. application Ser. No. 13/466,372, filed May 8, 2012, which claims priority to U.S. Provisional Application No. 61/525,581, filed Aug. 19, 2011, and is a Continuation of PCT International Application No. PCT/US12/51448, filed Aug. 17, 2012. The disclosures of these applications including the specifications, the drawings, and the claims are hereby incorporated by reference in their entirety.

FIELD

The present disclosure provides a weight loss composition and method. More specifically, the weight loss composition of the subject technology includes protein and fat, but is substantially free of carbohydrates.

BACKGROUND

The current way of life in most urbanized societies may be characterized by less physical work and increased consumption of fat, carbohydrates and proteins, resulting in the energy intake exceeding energy expenditure. This shift in the energy balance causes storage of energy in the body in the form of fat, leading to an increase of overweight and obesity, due to the long-term energy imbalance associated with lifestyle.

The percentage of overweight people increases year by year and obesity is a disease that is reaching epidemic proportions in some countries. The health risks associated with being overweight and obesity are numerous and it has been shown that these conditions contribute to morbidity and mortality of individuals suffering from diseases such as hypertension, stroke, diabetes mellitus type II, gallbladder disease and ischemic heart disease. The cosmetic perspective of body fat is also to be considered as the demand for dietary supplements or medicine to gain or maintain a leaner body is constantly increasing.

The pharmaceutical industry has developed drugs to help people lose weight. However, no drug has been discovered that allows individuals to eat all they desire and retain a sedentary lifestyle while simultaneously losing weight. Furthermore, the drug products available to the general public, whether by prescription or as over-the-counter preparations, are not free of risk. Known risks include valvular heart disease arising out of the use of the combination of fenfluramine and phentermine (Fen-Phen), and irregular heart beat (arrhythmia) that is associated with the use of phenylpropanolamine (PPA). These risks have resulted in bans on the use of these drugs in weight loss products and programs in some countries.

Health risks of anti-obesity preparations are not limited to prescription and/or over-the-counter medications. The use of ephedra in nutritional products employed for weight loss has been associated with arrhythmia and even sudden death in susceptible individuals.

A common strategy for reducing weight or for maintaining a normal body weight has been to reduce the average energy intake by lowering the dietary fat intake. However, the low- or non-fat and other diet products are far too often abandoned by the individual due to a reduced taste sensation, palatability and/or structure. To increase patient adherence to a non-fat diet regimen and promote a rapid weight loss, for example, a diet regimen termed "NEC" (Nutrizione Enterale Chetogena)—also known as "KEN" (Ketogenic Enteral Nutrition), or Dieta al Sondino, which in the U.S. is being marketed as "DietTube®"—has been devised which involves a nasogastric administration of a solution containing predominantly protein for a predefined period of about 10 days.

However, although the tube feeding of the diet composition in the NEC, KEN or DietTube® diet systems has been successful in inducing weight loss, still a significant portion of the patients using these or similar diets report being hungry. Therefore, there is still a need for a weight-loss product and method having the ability of reducing or postponing the sensation of hunger and/or appetite and perhaps at the same time being able to increase or prolong the feeling of satiety.

SUMMARY

In the subject technology, it has been found that the addition of an effective amount of fat to protein at certain ratios in a composition for nasogastric administration, is surprisingly effective in both inducing a rapid weight loss and significantly reducing or eliminating hunger.

The subject technology is illustrated, for example, according to various aspects described below.

In one aspect, the subject technology relates to a weight-loss composition including protein and fat; wherein the composition is substantially free of carbohydrates; and wherein the composition induces body weight loss when administered to a subject as the only source of nutrition for at least 12 hours. In an embodiment relating to this aspect, the fat comprises medium chain triglycerides (MCT) that is substantially free of long chain triglycerides (LCT) and/or small chain triglycerides (SCT); and the ratio of the MCT to the protein in the composition is in the range of about 0.05:1 to about 1:1 by weight, and this ratio synergistically reduces or eliminates hunger or induces satiety in the subject for a period of at least 12 hours. In another embodiment relating to this aspect, the composition induces an average body weight loss of greater than or equal to about 1% per day. In an embodiment relating to this aspect, the fat comprises LCT or SCT that is substantially free of the other two forms of triglycerides (i.e., MCT and SCT or MCT and LCT, respectively); and the ratio of the LCT or SCT to the protein in the composition is in the range of about 0.05:1 to about 1:1 by weight, and this ratio synergistically reduces or eliminates hunger or induces satiety in the subject for a period of at least 12 hours. In another embodiment relating to this aspect, the composition induces an average body weight loss of greater than or equal to about 1% per day.

In another aspect, the subject technology relates to a method of inducing body weight loss in a subject in need thereof, including administering to the subject a weight-loss composition comprising an effective amount of protein and an effective amount of fat, wherein the composition is substantially free of carbohydrates; and wherein the composition induces body weight loss in the subject when administered to the subject as the sole source of nutrition for a period of at least 12 hours. In an embodiment relating to this aspect of the subject technology, the fat comprises medium chain triglycerides (MCT) that is substantially free of long chain triglycerides (LCT) and/or small chain triglycerides (SCT); and the ratio of the MCT to the protein in the composition is in the range of about 0.05:1 to about 1:1 by weight, and this ratio synergistically reduces or eliminates hunger or induces satiety in the subject for a period of at least 12 hours. In another embodiment relating to this aspect, the method induces an average body weight loss of greater than or equal to about 1% per day. In an embodiment relating to this aspect, the fat comprises LCT or SCT that is substantially free of the other two forms of triglycerides (i.e., MCT and SCT or MCT and LCT, respectively); and the ratio of the LCT or SCT to the protein in the composition is in the range of about 0.05:1 to about 1:1 by weight, and this ratio synergistically reduces or eliminates hunger or induces satiety in the subject for a period of at least 12 hours. In another embodiment relating to this aspect, the composition induces an average body weight loss of greater than or equal to about 1% per day.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof.

It is to be understood that both the foregoing general description and the following detailed description are exemplary and explanatory and are intended to provide further explanation of the subject technology as claimed.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

The subject technology is predicated, at least in part, on the surprising finding that addition of an effective amount of fat (e.g., medium chain triglycerides (MCT)) to a predominantly protein diet for nasogastric administration not only does not reduce the effectiveness of the diet in reducing body weight, but also can promote a comparable or even greater body weight loss as compared to a diet that lacks fat or has a negligible amount of fat.

In addition, the subject technology is predicated, at least in part, on the surprisingly finding that in weight loss compositions of the instant disclosure, at certain ratios, the fat and protein can synergistically reduce and/or eliminate hunger in a subject to whom the composition is being administered.

Accordingly, in an aspect, the subject technology relates to a weight loss composition that includes protein and fat; wherein the composition is substantially free of carbohydrates; and wherein the composition induces body weight loss when administered to a subject as the only source of nutrition for at least 12 hours.

In another aspect, the subject technology relates to a method of inducing body weight loss in a mammal such as human, the method includes administering to a subject a weight-loss composition containing an effective amount of a protein and an effective amount of fat. The composition in this aspect is substantially free of carbohydrates. In addition, the composition induces body weight loss in the subject when administered to the subject as the sole source of nutrition for a period of at least 12 hours.

In certain embodiments, the weight loss composition of the subject technology is administered nasogastrically via a feeding tube. In certain embodiments, the weight loss composition of the subject technology is administered continuously throughout the treatment period. The treatment period may be any period from about 1 hour to 14 days. In other embodiments, the weight loss composition of the subject technology is administered intermittently, for example, every 1 to 24 hours, or any intervals in between, during the treatment period.

Both components (i.e., protein and fat) may be administered simultaneously, or they may be administered separately during the treatment period. In this embodiment, the fat may be administered as an oil, for example, while the protein may be administered as an aqueous solution. In certain embodiments, when the two components are administered separately, protein, for example, can be administered continuously while MCT is administered intermittently and in bolus every 1 to 24 hours, or vice versa.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa.

As stated above, the weight loss composition of the present disclosure is substantially free of carbohydrates. In this context, the term "substantially free of carbohydrates" means that the composition contains less than about 1.5% by weight of carbohydrates, including zero percent by weight of such ingredient. With respect to the triglycerides disclosed herein, the term "substantially free of" in the context of long chain, medium chain and/or small chain triglycerides means that the composition contains less than about 0.05% by weight of the specified triglycerides, including zero percent by weight of such ingredient.

As used herein, the term "fat" refers to triacylglycerides or triglycerides formed by the esterification reaction of long chain-, medium chain- or short chain-fatty acids with glycerol, a trihydroxy alcohol, or a mixture thereof, in any of solid, liquid or suspension forms, regardless of whether they are obtained from animal, fowl, fish or plants sources or are made synthetically, so long as they are safe for consumption by mammals, particularly humans. The fatty acid chains in biological systems usually contain an even number of carbon atoms, typically between 14 and 24, with the 16 (palmitate) and 18 (stearate) carbon fatty acids being the most common. Generally, triglycerides comprised of fatty acid chains with from 2 to 5 carbon atoms are referred to as short chain triglycerides ("SCT") and those with from 6 to 12 carbon atoms are referred to as medium chain triglycerides ("MCT"). Both SCT and MCT are often saturated and are found in dairy products as well as some plant oils. Those triglycerides comprised of fatty acid chains with 14 carbon atoms or greater are referred to as long chain triglycerides ("LCT"), may have points of unsaturation and are found in animal, fowl and fish products as well as plant oils.

In the context of the present disclosure, hunger is conveniently assessed by using a variation of visual analogue scales (VAS) as described in Flint et al. "Reproducibility, power and validity of visual analogue scares in assessment of appetite sensations in single test meal studies." Int. J. Obesity 24(1): 38-48 (2000), which is incorporated herein by reference its entirety. A scale of 0-4 (with zero being not at all hungry and 4 being as hungry as the subject has ever felt) was used to assess hunger in subjects using the composition and methods of the present disclosure.

As used herein, the phrase "the sole source of nutrition" refers to the composition of the subject technology being the only food a subject consumes during the treatment period. The subject may still consume water and unsweetened beverages, free of carbohydrates, to quench thirst; however no other food or nutrient should be consumed during the treatment period.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology.

Generally, weight gain is caused by consuming more calories than the body uses for its basal metabolic functions and additional activities in which an individual is involved. The human body stores these excess calories as fatty deposits (lipids in adipose tissue) throughout the body, but is not able to readily access these fatty deposits to satisfy energy needs. To use these stored lipids as an energy source, the number of calories ingested must be less than the total energy expenditure of the body (basal metabolic rate plus activity level). Under hypocaloric conditions the body consumes stored fat as a source of fuel.

Thus, a common practice for weight loss has been to limit fat and carbohydrate intake. However, a reduced fat and carbohydrate diet is usually unpalatable and unappetizing and induces further cravings for food that reduce adherence to weight loss regimens. As mentioned above, diet regimens such as NEC, KEN or DietTube® diets have been designed to deliver a predominantly protein diet directly to the stomach to overcome the palatability problems associated with such diets. However, such diets have not been able to totally eliminate hunger and cravings for food in patients using these regimens. Consequently, these diets often fail.

In the subject technology, however, it has surprisingly been found that a combination of fat and proteins administered, which is substantially free of carbohydrates, can synergistically act in reducing and/or eliminating hunger and promoting and/or prolonging satiety in subjects for at least 12 hours.

In addition, it has surprisingly been found that in the absence of the fat and protein in the compositions of the instant technology can synergistically induce ketosis in subjects, which results in more weight loss as compared with a composition that has no or a negligible amount of fat such as that in NEC, KEN or DietTube® diets.

Accordingly, the subject technology relates to a composition and method for the management of body weight. In the present context the term "management of body weight" covers all aspects of modulating the body weight for maintenance or achievement of a "desirable weight." In contrast to the "desirable weight" the expressions "overweight" and "obesity" are used as indications of a body with a weight exceeding the "desirable weight."

The "desirable weight", "normal weight" or "optimal weight" for humans may be defined according to standards such as Body Mass Index (BMI), which is a common measure expressing the relationship (or ratio) of weight-to-height (for definition see below). The BMI is more highly correlated with body fat than any other simple measure of height and weight. Desirable BMI levels may vary with age, but a "normal" BMI is considered to be in the range of 18.5-24.9.

The definition of "overweight" is an increased body weight in relation to height, when compared to a standard of acceptable or desirable weight. Individuals with BMI in the range of 25-29.9 are considered to be overweight.

Obesity is a multi-factorial disease involving an accumulation of excess adipose tissue (fat) sufficient to harm health. Obesity can cause the development of several diseases, and individuals who are significantly overweight or obese generally have a poor health status. Obesity is largely preventable through changes in lifestyle, especially diet. However, treatment may be desired and needed to aid in loosing of weight.

There are many types of obesity, but it is most commonly assessed by a single measure, the Body Mass Index (BMI) a ratio of weight and height (BMweight (kg)/height (m)$^2$). The World Health Organization classifies underweight, normal weight, overweight and obesity according to categories of BMI (cf. table below). This height independent measure of weight allows comparisons to be made more readily within and between populations. The BMI value, however, neither distinguish fat from lean tissue nor identify whether the fat is laid down in particular sites e.g., abdominally where it has more serious consequences. See Table 1.

Waist circumference measurement is also increasingly recognized as a simple means of identifying abdominal obesity. Body fat distribution can be estimated by skinfold measures, waist-to-hip circumference ratios, or techniques such as ultrasound, computed tomography, or magnetic resonance imaging.

TABLE 1

| Classification | BMI (kg/m$^2$) | Risk of co-morbidities |
| --- | --- | --- |
| Underweight | <18.5 | Low (but risk of other clinical problems increased) |
| Normal range | 18.5-24.9 | Average |
| Overweight* | ≥25 | |

TABLE 1-continued

| Classification | BMI (kg/m²) | Risk of co-morbidities |
|---|---|---|
| Pre-obese | 25.0-29.9 | Mildly increased |
| Obese | >30.0 | |
| Class I | 30.0-34.9 | Moderate |
| Class II | 35.0-39.9 | Severe |
| Class III | >40.0 | Very Severe |

*The term overweight refers to a BMI ≥25, but is frequently and also in the present specification and claims adapted to refer to the BMI 25-29.9, differentiating the pre-obese from the obese categories As illustrated in Table 1 above, the severities of obesity may by classified by ranges of BMI where BMI in the range of 30-34.9 is classified as moderate obesity, BMI in the range of 35-39.9 is classified as severe obesity and BMI over 40 is classified as very severe obesity. The definition of obesity may also include taking into account both the distribution of fat throughout the body and the size of the adipose tissue deposits.

Individuals falling under the above characterization as "obese" are far more susceptible to health implications as a consequence of their overweight. Several serious medical conditions have been linked to obesity, including type 2 diabetes, heart disease, high blood pressure, and stroke. Obesity is also linked to higher rates of certain types of cancer. Obese men are more likely than non-obese men to die from cancer of the colon, rectum, or prostate. Obese women are more likely than non-obese women to die from cancer of the gallbladder, breast, uterus, cervix, or ovaries. Other diseases and health problems linked to obesity include gallbladder disease and gallstones, liver disease, osteoarthritis, a disease in which the joints deteriorate possibly as a result of excess weight on the joints, gout, another disease affecting the joints, pulmonary (breathing) problems, including sleep apnea in which a person can stop breathing for a short time during sleep, reproductive problems in women, including menstrual irregularities and infertility. Health care providers generally agree that the more obese a person is the more likely he or she is to develop health problems.

The expression "cosmetic overweight" refers to a weight that does not have any immediately medical implications on the individual but may be in a range that is not satisfactory for cosmetic reasons. As fashion with respect to body size changes some individuals may interpret the "normal weight" as "cosmetic overweight." As a consequence such individuals may have a desire for treating cosmetic overweight.

The subject technology provides compositions and methods for weight loss, the management of body weight, and the maintenance or achievement of a desirable weight in a subject in need thereof. In addition, the compositions and methods of the subject technology can be used to treat physical, physiological or psychological diseases or conditions associated with obesity and/or excess body weight.

In one aspect, the weight loss composition of the subject technology provides a ketogenic diet for the treatment of obesity and/or for weight management. The ketogenic diet includes protein and fat, and is substantially free of carbohydrates. The ketogenic diet (also known as the K-E diet) can be used for complete nourishment of a subject for at least 12 hours, without significant concomitant hunger and food cravings. In an embodiment relating to this aspect, the weight loss composition of the subject technology may have use for the treatment of conditions or diseases (e.g., diabetes, metabolic syndrome or hypertriglyceridaemia) for which a ketogenic diet is beneficial.

The weight loss formulations of the subject technology are especially suitable for inducing rapid weight loss in a subject in need thereof. In certain embodiments, the weight loss composition of the subject technology is in dry form but is reconstituted in an aqueous solution prior to nasogastric administration. In certain other embodiments, the weight loss composition of the subject technology can be administered orally (e.g., by ingestion or orogastrically). Components such as vitamins, minerals, diluents or carriers may also be present in the composition of the subject technology. Accordingly, the compositions of the subject technology may include one or more pharmaceutically acceptable carrier(s), diluents(s) and/or excipient(s). The carrier, diluent and/or excipient must be "acceptable" in the sense of being compatible with the other ingredients of the composition and not deleterious to the recipient thereof.

As used herein, and discussed elsewhere herein, proteins suitable for use in the compositions and methods of the subject technology include, but are not limited to, intact or hydrolyzed whey protein, egg protein including egg albumen, lactalbumin, casein, soy protein polypeptides or peptides or amino acids (PPAA) and their derivatives from various biological sources, and are substantially free of carbohydrates. In certain embodiments, the compositions of the subject technology include a single type of protein. In other embodiments, the protein content of the compositions of the subject technology can include more than type of protein or can include a mixture of two or more different proteins, each of which can independently exist in an intact or hydrolyzed form or both.

Whey protein comprises a protein fraction obtained from the milk of cows. Cow milk contains two major protein fractions, including casein, which comprises about 80% of the total protein, and whey protein, which comprises about 20% of the total protein. Whey protein includes several proteins, including, for example, β-lactoglobulin, α-lactoglobulin, immunoglobulins, and lactoferrin. Whey protein is more soluble than casein and also has a higher quality rating.

Whey protein is available as "whey protein concentrate", which contains about 29% to 85% whey protein, and "whey protein isolate", which contains 90% or more whey protein and little, if any, fat, cholesterol, or carbohydrates (e.g., Lactose). Regardless of the source of whey protein, the final concentration of whey protein in powder or liquid forms is about 25% to 99%. In an embodiment, the compositions of the subject technology comprise whey protein isolate.

Whey protein contains essential and semi-essential amino acids, including cationic amino acids (e.g., Lysine, Arginine, and Histidine) and proteins and, therefore, is a high nutritional quality source of protein. Proteins of high nutritional value may be defined as proteins that contain high concentrations of essential and semi-essential amino acids, including hydrophobic amino acids (Leucine, Isoleucine, Methionine, Phenylalanine, Tryptophan, Valine), hydroxylated amino acids (Threonine) and hydrophilic amino acids that are positively charged (Lysine, Arginine, and Histidine). Whey protein also has a very high biological value, which is a measure of percent assimilation into the body. It can be a particularly valuable source of high-value nutrition for athletes and for individuals with special medical needs (e.g., lactose intolerant individuals), and can be a valuable component of diet programs. Further, whey protein contains biologically active proteins such as immunoglobulins and lactoferrin and, therefore, provides advantages over other protein sources such as soy protein. Whey protein also has a fresh, neutral taste.

Egg protein also contains essential and semi-essential amino acids, including cationic (basic) amino acids and proteins and, therefore, is a high nutritional quality source of protein. Egg protein also has a very high biological value, and thus may be found in various embodiments of high protein compositions and dietary supplements.

In an embodiment, the effective amount of a protein used in compositions and methods of the subject technology is an amount that together with fat induces weight loss in a subject. As discussed herein above, such effective amount of the protein can be determined in light of disclosed blood ketone levels, urine ketone levels or weigh loss measurements (e.g., BMI or body weight measurements before and after the treatment). In certain embodiments, the ratio of fat to protein in the compositions of the subject technology is in the range of about 0.05:1 to about 1:1 by weight. In this context, the daily (24-hour) protein dose is about 1.0 g/kg/day to about 3.0 g/kg/day. Alternatively, the daily protein dose can be in the range of about 1.3 g/kg/day to about 2.5 g/kg/day of protein. In certain embodiments, a daily (24-hour) dose of the composition of the subject technology, for nasogastric administration, includes one or more proteins in a total amount of about 100 to about 150 grams, or any specific number within that range. In certain embodiments, the daily dose of protein is about 108-135 grams, or any specific number within that range. In certain other embodiments, the daily dose of protein is at least about 1 g/kg/day, at least about 1.5 g/kg/day, at least about 2 g/kg/day, at least about 2.5 g/kg/day, at least about 3 g/kg/day, at least about 4 g/kg/day, at least about 5 g/kg/day, at least about 10 g/kg/day, at least about 15 g/kg/day, at least about 20 g/kg/day, at least about 30 g/kg/day, at least about 40 g/kg/day, or at least about 50 g/kg/day.

In an embodiment, the effective amount of protein for use in compositions and methods of the subject technology is an amount that together with fat of the composition synergistically induces ketosis and in turn weight loss in a subject. Ketosis and weight loss occur when the instant composition is the sole source of nutrition for at least 12 hours. In a related embodiment, the composition further reduces or eliminates hunger for at least 12 hours. As discussed herein above, such effective amount of a protein can be determined in light of blood ketone levels, urine ketone levels or weigh loss measurements.

In an embodiment, the effective amount of a protein for use in compositions and methods of the subject technology is an amount that together with fat of the composition synergistically reduces or eliminates hunger in a subject. This synergy occurs when the composition is administered to a subject as the only source of nutrition for at least 12 hours. As discussed herein above, such effective amount of a protein can be determined in light of hunger assessments using visual analogue scales (VAS) as described in Flint et al. (2000) or a variation thereof.

In an embodiment, the weight loss composition of the subject technology includes an amount of protein, which can be at least, greater than, equal to, or any number in between 5%, 10%, 15%, 20%, 25%, 30%, 35%, 40%, 45%, 50%, 55%, 60%, 65%, 70%, 75%, 80%, 85%, 90%, or 95% w/w or w/v protein). In another embodiment, the weight loss composition of the subject technology provides a daily dosage of protein in an amount of about 100 to 150 grams. Alternatively, the weight loss composition of the subject technology provides a daily dosage of protein in an amount equal to or greater than 60 grams, 80 grams, 100 grams, 110 grams, 120 grams, 130 grams, 140 grams or 150 grams, or any number in between. In an embodiment, the weight loss composition of the subject technology provides a daily dosage of protein in an amount of about 108-135 grams.

As used herein, and discussed elsewhere herein, the fat suitable for use in the compositions and methods of the subject technology include long chain triglycerides (LCT), short chain triglycerides (SCT) and/or medium chain triglycerides (MCT). The fat component can be any triglycerides (in liquid form (e.g., oil), solid form (e.g., fat or powder), or suspension) known in the art to be suitable for use in nutritional compositions. Typical fats include those from animal or plant sources such as, for example, milk fat, safflower oil, canola oil, egg yolk lipid, olive oil, cotton seed oil, coconut oil, hazelnut oil, palm oil, palm kernel oil, and/or rapeseed oil. The fat may consist of saturated, unsaturated, mono-, di-, tri- or polyunsaturated fatty acids. Unsaturated fatty acids may be n-3 or n-6 fatty acids. In certain embodiments, the fat component contains primarily or solely one form of fat, i.e., MCT, LCT or SCT.

The short chain triglycerides suitable for use in the subject technology are preferably those comprising from 2 to 5 carbon atoms, which may be either saturated or unsaturated, straight or branched. They may be derived from any synthetic or natural organic acid, including, but not limited to butyric (butanoic), valeric (pentanoic), glycolic (hydroxyacetic), lactic (2hydroxypropanoic), hydracrylic (3-hydroxypropanoic), hydroxybutyric, hydroxypentanoic and the like acids As used herein, chemical names include isomeric variations: for example, "butyric acid" includes normal butyric acid (butanoic) and iso-butyric (2methylbutanoic acid), "valeric acid" includes normal valeric acid and iso-valeric (3methylbutanoic) as so forth. The preferred fatty acids are butyric or mixtures of these.

Mixtures of short chain fatty acids may be derived from unhydrogenated, partially hydrogenated or fully hydrogenated dairy butterfat, coconut, palm kernel and the like oils.

The medium chain residues are preferably those comprising from 6 to 14 carbon atoms, more preferably from 6 to 10 carbon atoms and most preferably from 8 to 10 carbon atoms. They include, but are not limited to, C6 (caproic acid), C8 (caprylic acid), C10 (capric acid) and C12 (lauric acid) as well as mixtures thereof. The most preferred medium chain fatty chain comprises lipoic or thioctic acid in any one of its forms including alpha-lipoic acid.

The long chain residues may de derived from any synthetic or natural, straight or branched, saturated or unsaturated, organic acid including, but no limited to paimitic (hexadecanoic), stearic (octadecanoic), arachidic (eicosanoic), behenic (docsanoic), lignoceric (tetracosanoic), cerotic (hexacosanoic), montanic (octacosanoic), melissic (triaconanoic) and the like acids. They may also be derived by hydrogenating an unsaturated acid, including, but not limited to palmitoleic (9-hexadecenoic), oleic (cis 9octadecenoic), elaidic (trans-9-octadecenoic), vaccenic (trans-11-octadecenoic), linoleic (cis, cis-9,12-octadecenoic), linolenic (9,12,15-octadecatrienoic and 6,9,12octadecatrienoic), eleostearic (9,11,13-octadecatrienoic), arachidonic (5,8,11,14eicosatetraenoic), nervonic (cis-15-tetracosenoic), eicosapentanoic, docosatetraenoic, docosapentaenoic, docosahexaenoic, and the like acids. Chemical names include isomeric variations.

The long chain residues may be derived from, for example, non-hydrogenated, partially hydrogenated or fully hydrogenated oils such as soybean, safflower, sunflower, high oleic sunflower, sesame, peanut, corn, olive, rice bran, babassu nut, palm, mustard seed, cottonseed, poppyseed, low or high erucic rapeseed, shea, marine, meadowfoam, and the like oils. Alternatively, the long chain residues may be derived from tallow, lard, shea butter, dairy butter, jojoba and mixtures thereof. Suitable long chain (C14-C22) triglycerides for use in the subject technology include, but are not limited to, arachis oil, soya bean oil, castor oil, corn oil, safflower oil, olive oil, apricot kernel oil, sesame oil, cotton seed oil, sunflower seed oil, palm oil and rapeseed oil.

In an embodiment, the fat suitable for use in the subject technology comprise one or more omega-3 polyunsaturated fatty acids ("omega-3 PUFA's) or derivatives thereof. The omega-3 PUFAs (C18:3n3) for use within the composition of the subject technology are selected from alpha-linolenic acid, EPA and DHA in the form of, inter alia, fatty acids, triglycerides, phospholipids, esters or free fatty acid salts.

In one embodiment of the subject technology, the omega-3 PUFAs may be extracted from zooplankton, fish or other marine animals using suitable bioconcentration techniques. In the alternative, omega-3 PUFAs may be synthesized using microalgae as the source material. In one preferred form, marine fish oil may be mixed directly with SCT and MCT components to form fat mixture suitable for use in the subject technology. The marine oil may be extracted by techniques known in the art from, inter alia: finfish such as cod, salmon, tuna, herring, halibut, shark, catfish, pollock, dogfish, anchovy, mackerel, trout, and eel; animals such as seals and whales; crustaceans such as crabs, clams and lobster; mollusks and the like.

Without limiting the generality of the foregoing, the preferred marine sources of omega-3 PUFAs are as follows: salmon (sockeye), tuna, salmon (pink), shark, dogfish, halibut, anchovy, salmon (Atlantic), mackerel (Atlantic), salmon (Pacific), spanish sardine, trout (rainbow), mackerel (Pacific), and swordfish (herring). Alternatively, plant sources of omega-3 PUFAs may be used. The great advantage of plant sources may be reduced odour as compared to some marine sources. Plant sources include, but are not limited to, plant oils such as hemp oil, flaxseed oil linseed oil and corn oil as well as soy. The most preferred plant-derived sources are flax seed oil and linseed oil.

Suitable medium chain triglycerides (MCTs) for use in the subject technology include but are not limited to, MCTs represented by the following formula:

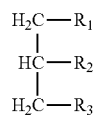

wherein R1, R2, and R3 are independently selected from the group consisting of a fatty acid residue esterified to a glycerol backbone having 6-12 carbons in the carbon backbone ($C_6$ to $C_{12}$ fatty acids), a saturated fatty acid residue esterified to a glycerol backbone having 6-12 carbons in the carbon backbone ($C_6$ to $C_{12}$ fatty acids), an unsaturated fatty acid residue esterified to a glycerol backbone having 6-12 carbons in the carbon backbone ($C_6$ to $C_{12}$ fatty acids), and derivatives of any of the foregoing. The structured lipids of this subject technology may be prepared by any process known in the art, such as direct esterification, rearrangement, fractionation, transesterification, or the like. For example the lipids may be prepared by the rearrangement of a vegetable oil such as coconut oil. Exemplary MCTs include caproic triglyceride, caprylic triglyceride, capric triglyceride, myristic triglyceride or lauric triglyceride, which can be extracted or derived from plant sources such as, for example, coconut oil or palm kernels.

In an embodiment, the compositions and methods of the subject technology comprise the use of MCT wherein R1, R2, and R3 are fatty acids containing a six-carbon backbone (tri-C6:0). Tri-C6:0 MCTs are absorbed very rapidly by the gastrointestinal tract in a number of animal model systems. In another embodiment, the method comprises the use of MCTs wherein R1, R2, and R3 are fatty acids containing an eight-carbon backbone (tri-C8:0). In another embodiment, the method comprises the use of MCT wherein R1, R2, and R3 are fatty acids containing a ten-carbon backbone (tri-C10:0). In another embodiment, the method comprises the use of MCT wherein R1, R2, and R3 are a mixture of C8:0 and C10:0 fatty acids. In another embodiment, the method comprises the use of MCT wherein R1, R2 and R3 are a mixture of C6:0, C8:0, C10:0, and C12:0 fatty acids.

In another embodiment, greater than 95% of R1, R2 and R3 carbon chains of the MCT are 8 carbons in length. In yet another embodiment, the R1, R2, and R3 carbon chains are 6-carbon or 10-carbon chains. In another embodiment, 50% of the R1, R2 and R3 carbon chains of the MCT are 8 carbons in length and about 50% of the R1, R2 and R3 carbon chains of the MCT are about 10 carbons in length. Additionally, utilization of MCT can be increased by emulsification. Emulsification of lipids increases the surface area for action by lipases, resulting in more rapid hydrolysis and release of medium chain fatty acids (MCFA). Methods for emulsification of these triglycerides are well known to those skilled in the art. Additional information about MCTs are provided in, for example, U.S. Pat. No. 8,124,589, which is hereby incorporated by reference it its entirety.

In another embodiment, the preferred short, medium and long chain triglycerides may be isolated from natural or processed fats or oils, or fractions thereof using techniques known in the art.

"Designer" fats are also within the scope of the subject technology, what is essentially achieved is the formation of the fat component of the subject technology which maximize dietary and therapeutic efficacy. For example, the fat component of the compositions of the subject technology can be solely an LCT or MCT or SCT, but substantially free of the other two types of triglycerides. Alternatively or in addition, the fat component can be a mixture of various LCTs or various MCTs or various SCTs. Alternatively or in addition, the fat component can be a mixture of one or more LCTs and one or more MCTs, but substantially free of SCTs. Alternatively or in addition, the fat component can be a mixture of one or more LCTs and one or more SCTs but substantially free of MCTs. Alternatively or in addition, the fat component can be a mixture one or more MCTs and one or more SCTs but substantially free of LCTs. Alternatively or in addition, the fat component can be a mixture one or more LCT, one or more MCT and one or more SCT. Alternatively or in addition, the fat component can be any combinations of at least two of LCT, MCT or SCT, wherein each triglyceride can in turn include a single LCT, MCT or SCT or a mixture of LCTs, MCTs or SCTs.

In an embodiment, the effective amount of fat used in compositions and methods of the subject technology is an amount that together with the protein(s) of the composition induces weight loss in a subject. As discussed herein above, such effective amount of fat can be determined in light of blood ketone levels, urine ketone levels or weigh loss measurements. In certain embodiments, the ratio of fat to protein in the compositions of the subject technology is in the range of about 0.05:1 to about 1:1 by weight. In this context, a daily (24-hour) fat dose in the composition is about 0.05 g/kg/day to about 3 g/kg/day. In other embodiments, the fat daily dose is in the range of about 0.1 g/kg/day to about 2.5 g/kg/day. In other embodiments, the daily dose of fat is at least about 0.05 g/kg/day, at least about 0.1 g/kg/day, at least about 0.15 g/kg/ day, at least about 0.2 g/kg/day, at least about 0.5 g/kg/day, at least about 1 g/kg/day, at least about 1.5 g/kg/day, at least about 2 g/kg/day, at least about 2.5 g/kg/day, at least about 3 g/kg/day, at least about 4 g/kg/day, at least about 5 g/kg/day, at least about 10 g/kg/day, at least about 15 g/kg/day, at least about 20 g/kg/day, at least about 30 g/kg/day, at least about 40 g/kg/day, or at least about 50 g/kg/day. In certain embodiments, a daily (24-hour) dose of the composition of the subject technology, for nasogastric administration, includes fat in a total amount of about 50 to about 150 grams, or any specific number within that range. In certain embodiments, the daily dose of fat is about 108-135 grams, or any specific number within that range.

In an embodiment, the effective amount of a fat (e.g., MCT) used in compositions and methods of the subject technology is an amount that together with the protein(s) of the composition synergistically induces ketosis and in turn weight loss in a subject. The ketosis occurs when the composition is administered to a subject as the only source of nutrition for at least 12 hours. In a related embodiment, the composition further reduces or eliminates hunger for at least 12 hours. As discussed herein above, such effective amount of fat can be determined in light of blood ketone levels, urine ketone levels or weigh loss measurements.

In an embodiment, the effective amount of fat (e.g., MCT) used in compositions and methods of the subject technology is an amount that together with the protein(s) of the composition synergistically reduces or eliminates hunger in a subject. This synergy occurs when the composition of the subject technology is administered to a subject as the only source of nutrition for at least 12 hours. As discussed herein above, such effective amount of fat can be determined in light of hunger assessments using visual analogue scales (VAS) as described in Flint et al. (2000) or a variation thereof. In an embodiment, the daily fat dose is about 0.1 g/kg/day to about 1.5 g/kg/day.

In an embodiment, the weight loss composition of the subject technology includes an amount of fat, which can be at least, greater than, equal to, or any number in between 2%, 5%, 10%, 15%, 20%, 25%, 30%, 35%, 40%, 45%, 50%, 55%, 60%, 65%, 70%, 75%, 80%, 85%, 90%, or 95% w/w or w/v fat). In another embodiment, the weight loss composition of the subject technology provides a daily dosage of fat in an amount of about 10 to 150 grams. Alternatively, the weight loss composition of the subject technology provides a daily dosage of fat in an amount equal to or greater than 5 grams, 7 grams, 10 grams, 20 grams, 30 grams, 40 grams, 50 grams, 60 grams, 80 grams, 100 grams, 110 grams, 120 grams, 130 grams, 140 grams or 150 grams, or any number in between. In an embodiment, the weight loss composition of the subject technology provides a daily dosage of fat in an amount of about 5-150 grams. In an embodiment, the weight loss composition of the subject technology provides a daily dosage of fat in an amount of about 10 grams. In an embodiment, the weight loss composition of the subject technology provides a daily dosage of fat in an amount of about 90 grams.

The compositions of the subject technology can be administered to a subject enterally. Preferably, the compositions are administered orogastrically and/or nasogastrically via a feeding tube. In an embodiment, the weight loss compositions of the subject, technology are administered continuously or intermittently. In an embodiment, the composition of the present disclosure is administered to a subject in need thereof as the sole source of nutrition for a period of at least 12 hours, at least one day (24 hrs), at least 3 days, at least 5 days, at least 7 days or at least 9 days.

In an embodiment, the composition of the subject technology also includes one or more vitamins and/or minerals. For example, sufficient vitamins and minerals may be provided to supply about 25% to about 250% of the recommended daily allowance of the vitamins and minerals per 1000 calories of the nutritional composition. In addition, the composition preferably has an osmolarity of about 200 mOsm/l to about 400 mOsm/l; for example about 250 mOsm/l to about 350 mOsm/l.

In an embodiment, the composition of the subject technology is in the form of a ready-to-use formulation. In this form, the composition may be fed to a patient via a nasogastric tube, jejunum tube or by having the patient drink it. In an alternative embodiment, the composition is in soluble powder form for reconstitution prior to use.

In an embodiment, the formulations provide daily doses of the compositions of the subject technology. In an embodiment, the subject technology provides a formulation comprising a mixture of protein and fat to provide weight loss when administered to a subject as the only source of nutrition for a period of at least 12 hours. In a related embodiment, the formulation of the subject technology is substantially free of carbohydrates. In certain embodiments, the ratio of fat to protein in the formulations of the subject technology is in the range of about 0.05:1 to about 1:1 by weight. In an embodiment, this ratio is about 0.1:1 by weight, about 0.15:1 by weight, about 0.25:1 by weight, about 0.35:1 by weight, about 0.45:1 by weight, about 0.55:1 by weight, about 0.65:1 by weight, about 0.75:1 by weight, about 0.85:1 by weight, or about 0.95:1 by weight.

In an embodiment, a formulation of the subject technology comprises a range of about 5 to about 150 g of emulsified fat combined with about 100 to about 150 g of a protein. Amounts of fat can be at least about 5 g, at least about 10 g, at least about 50 g or at least about 100 g. Amounts of protein can be at least about 50 g, at least about 100 g or at least about 150. For example, an exemplary daily dosage form of the subject technology can contain 10 g MCT (99% triC8:0) emulsified with 100 g of whey protein. Such a formulation is well tolerated and generally induces hyperketonemia for 3-4 hours in healthy human subjects.

In certain embodiments, the composition of the subject technology further includes one or more pharmaceutical compounds such as anti-bloating or anti-diarrheal agent. In certain other embodiments, the composition of the subject technology further includes pharmaceutically acceptable additives or diluents.

In an embodiment, the composition of the subject technology is produced according to a conventional method; for example, by blending together the protein source and a fat source. Emulsifiers may be included in the blend. Vitamins and/or minerals may be added, but are usually added later to avoid thermal degradation. Lipophilic vitamins, emulsifiers or the like may be dissolved into the lipid source prior to blending. Water, preferably water which has been subjected to reverse osmosis, may be mixed in to form a liquid mixture. The temperature of the water can be about 50° C. to about 80° C. to aid dispersal of the ingredients. Commercially available liquefiers may be used to form the liquid mixture.

The liquid mixture may be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger; for example a plate heat exchanger.

Preferably the liquid mixture is cooled to about 60° C. to about 85° C.; for example by flash cooling. The liquid mixture may be homogenised; for example in two stages at about 7 MPa to about 40 MPa in the first stage and about 2 MPa to about 14 MPa in the second stage. The homogenised mixture may be further cooled to add any heat sensitive components; such as vitamins and minerals. The pH and/or solids content of the homogenised mixture is conveniently standardized.

To produce a liquid product, the homogenised mixture is preferably aseptically filled into suitable containers. Aseptic filling of the containers may be carried out by pre-heating the homogenised mixture (for example to about 75 to about 85° C.) and injecting steam into the homogenised mixture to raise the temperature to about 140 to about 160° C.; for example at about 150° C. The homogenized mixture may be cooled, for example by flash cooling, to a temperature of about 75 to about 85° C. The homogenised mixture may be further homogenised, cooled to about room temperature and filled into containers. Suitable apparatus for carrying out aseptic filling of this nature is commercially available. To produce a powder product, the homogenised mixture is preferably dried to powder; for example by spray drying. Preferably, conventional procedures are used.

In an embodiment, the composition of the subject technology in liquid form is administered by tube feeding, by gravity, or pump. In this form, the composition may have a viscosity of less than about 12 cp at room temperature.

In an embodiment, the composition of the subject technology is suitable for clinical use. Furthermore, the composition is preferably suitable for patients with normal digestive function.

It will be appreciated that the composition may be in a form other than that suitable for clinical nutrition. For example, the composition may be in the form of a dessert, cereal, yoghurt, snack bar, or the like. If fed to pets, the enteral composition may be in the form of dried kibble, meat emulsion, or formulated emulsion.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

EXAMPLES

A better understanding of the subject technology may be obtained through the following examples which are set forth to illustrate, but are not to be construed as the limit of the subject technology.

Example 1

Preparing the Patient for Insertion of the Nasogastric Tube

No fasting is necessary prior to insertion of the gastrointestinal tube. As a preliminary procedure, the patient's nostril that is clearer is identified and sprayed with 2 sprays of phenylephrine 1% (Neo-Synephrine® Nose Spray). After at least 5 minutes, the patient is instructed to rapidly "sniff" approximately 2.5 ml of lidocaine jelly 2% from a 3 ml syringe with no needle. The patient should feel the lidocaine jelly coat the entire nostril to the back of the throat and swallow the jelly. The lidocaine jelly is then allowed to anesthetize the nasal mucosa, which could take at least 10 minutes.

Example 2

Insertion of the Gastrointestinal Tube

All necessary equipment should be prepared, assembled and available at the bedside prior to insertion the gastrointestinal tube. Basic equipment includes: universal precautions; the gastrointestinal tube which should be flushed with 3 mL water before inserting the stylet; 2% lidocaine jelly; adhesive film such as Tegaderm®, stethoscope; cup of water with ice chips and straw; emesis basin available if needed.

For safety reasons, the patient is instructed to sit in a 90 degrees angel. The patient should hold a large cup of cold water with both hands with a straw in the mouth. Before insertion, the feeding tube is dipped in water to activate the lubricant and lidocaine jelly is applied to the tip. Slowly, the tube is inserted into the anesthetized nostril and into the posterior nasopharynx. Occasionally, resistance may be encountered due to the nasal turbinates. Gentle repositioning of the direction of the tube will overcome the obstruction. The patient must be asked to rapidly swallow water as the tube is advancing into the esophagus. The tube is advanced when the patient swallows. If the tube is advanced when the patient inhales, the tube may enter the larynx instead of the esophagus and cause coughing. The tube is continuously advanced as the patient swallows water until the tube reaches the stomach or until about 12-14 inches of the tube remains outside of the tip of the nose. The positioning of the tube in the patient stomach can be confirmed by injecting 10 mL of air in the tube with a stethoscope over the stomach. The tube is then fastened to the cheek and passed behind the ear and again fastened to the neck with transparent film dressing.

Example 3

Weight Loss Studies

This example relates to the effect of an exemplary composition of the subject technology on body weight in a human subject.

An exemplary composition of the subject technology (See Table 2) is nasogastrically administered to a healthy female subject of 38 years of age.

TABLE 2

A daily dosage formulation (to be reconstituted in 2 Liters of water) for 24 hrs nasogastric administration

| Component | Amount | | % Daily Value |
|---|---|---|---|
| Protein (whey protein isolate) | 100-150 | g | Varies |
| MCT (from coconut oil) | 10-150 | g | Varies |
| Vitamin A | 5000 | IU | 100% |
| Vitamin C | 3 | mg | 100% |
| Vitamin D | 4 | mg | 100% |
| Vitamin E | 40 | mg | 100% |
| Vitamin B1 | 4 | mg | 100% |
| Vitamin B2 | 800 | mcg | 100% |
| Niacin | 12 | mcg | 100% |
| Vitamin B6 | 60 | mcg | 100% |
| Folic Acid | 10 | mg | 100% |
| Vitamin B12 | 3 | mg | 100% |
| Biotin | 4 | mg | 100% |
| Pantothenic Acid | 20 | mg | 100% |
| Calcium | 4 | mg | 2% |
| Phosphorous | 800 | mcg | 8% |
| Potassium | 12 | mcg | 2% |
| Chloride | 60 | mcg | 2% |

The composition above promoted a comparable or even greater body weight loss as compared to a diet that lacks MCTs. See Table 3 for the weight loss results in this subject.

TABLE 3

10-day weight loss test results

| DAY | WEIGHT | URINE KETONES | HUNGER (0-4) |
|---|---|---|---|
| 1 | 182 | NEG | 0 |
| 2 | | 15 | 0 |
| 3 | | 15 | 0 |
| 4 | | 50 | 0 |
| 5 | | 50 | 0 |
| 6 | 172 | 50 | 0 |
| 7 | | 150 | 0 |
| 8 | | 150 | 0 |
| 9 | | 150 | 0 |
| 10 | 163 | 150 | 0 |

As shown in Table 3, the subject lost more than 10 percent of her body weight in 10 days.

Example 4

Hunger Studies

In a separate study, the effects of the compositions of the subject technology on hunger sensation were tested. In this study, at three separate times (at least 12 hours apart), a human subject was nasogastrically given three formulations listed in three columns shown below. See Table 4. The subject was not informed of the nature or contents of each formulation but was asked to describe her hunger sensation on a scale of 0-4 with zero being not hungry at all and 4 being extremely hungry or as hungry as the subject had ever felt.

TABLE 4

Hunger Assessments Results

| | THE K-E DIET FORMULA | | PROTEIN FORMULA ONLY | | MCT OIL ONLY | |
|---|---|---|---|---|---|---|
| | URINE KETONES | HUNGER (0-4) | URINE KETONES | HUNGER (0-4) | URINE KETONES | HUNGER (0-4) |
| DAY 1 | NEG (after 6 hours of starting) | 0 | NEG (after 6 hours of starting) | 3 | NEG (after 6 hours of starting) stopped due to extreme hunger | 4 |
| DAY 2 | 15 | 0 | 15 | 4 | | |
| DAY 3 | 50 | 0 | 15 | 3 | | |

As shown in Table 4, it was surprisingly found that the MCT and protein components of the weight loss composition of the instant disclosure can synergistically reduce and/or eliminate hunger throughout the treatment period.

Example 5

Weigh Loss Studies

This example discloses the use of compositions and methods of the subject technology for promoting weight loss in human subjects. In this study, a daily (24-hour) dose of an exemplary composition of the subject technology (the K-E diet) was nasogastrically administered to eleven human subjects for a period of 10 days. Weights of the subjects before and after the diet program were measured which are shown in Table 5 below. The level of hunger was also determined in these individuals on a daily basis, whose average for each individual is provided in Table 5.

TABLE 5

The Weight Loss Results of the K-E Diet Being Administered Nasogastrically

| Patient No. | WT Before | WT After | WT Loss | % | Hunger |
|---|---|---|---|---|---|
| 1 | 153 | 138 | 15 | 10% | 0 |
| 2 | 182 | 162 | 20 | 11% | 0 |
| 3 | 242 | 218 | 24 | 10% | 1 |
| 4 | 172 | 155 | 17 | 10% | 1 |
| 5 | 184 | 164 | 20 | 11% | 0 |
| 6 | 164 | 148 | 16 | 10% | 0 |
| 7 | 142 | 125 | 17 | 11% | 0 |
| 8 | 195 | 172 | 23 | 12% | 0 |
| 9 | 205 | 183 | 22 | 10% | 1 |
| 10 | 176 | 156 | 20 | 11% | 0-1 |
| 11 | 227 | 202 | 25 | 11% | 0 |

As indicated by the percent weight loss in these eleven subjects, the K-E diet on average results in weight loss of 1% per day or higher, which is significantly greater than that promoted by compositions that lack MCTs.

The foregoing description is provided to enable a person skilled in the art to practice the various configurations described herein. While the subject technology has been particularly described with reference to the various tables, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

Although the subject technology has been described with reference to the examples provided above, it should be understood that various modifications can be made without departing from the spirit of the subject technology.

What is claimed is:

1. A method for treating a disorder or disease associated with obesity or excess body weight in a patient in need thereof comprising administering to the patient a composition comprising protein and fat; wherein the composition comprises less than about 1.5% by weight carbohydrates and less than about 0.05% by weight long chain triglycerides (LCT) and less than about 0.05% by weight short chain triglycerides (SCT); wherein the fat and protein comprises a ratio of 0.05:1 to 1:1 by weight medium chain triglycerides (MCT) to protein.

2. The method of claim 1, wherein the disorder or disease is selected from diabetes, metabolic syndrome and hypertriglyceridaemia.

3. The method of claim 1, wherein the disorder or disease is metabolic syndrome.

4. The method of claim 1, wherein the composition is in a liquid dosage form for administration to a subject through a nasogastric feeding tube, an orogastric feeding tube or a jejunum tube.

5. The method of claim 1, wherein the composition provides a dosage of the protein in an amount of from 60 to 150 g.

6. The method of claim 1, wherein the composition further comprises a component selected from the group consisting of vitamins, minerals, essential amino acids, and combinations thereof.

7. The method of claim 1, wherein the composition is administered continuously or intermittently throughout a course of treatment.

8. The method of claim 1, wherein the MCT comprises at least one of a medium chain triglyceride of the formula:

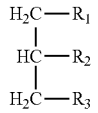

wherein the R1, R2, and R3 esterified to the glycerol backbone are each independently fatty acids comprising a 6-12 carbon chain.

9. The method of claim 8, wherein the MCT comprises at least one of caproic triglyceride, caprylic triglyceride, capric triglyceride or lauric triglyceride.

10. A method for treating diabetes type II in a patient in need thereof comprising administering to the patient a composition comprising protein and fat; wherein the composition comprises less than about 1.5% by weight carbohydrates and less than about 0.05% by weight long chain triglycerides (LCT) and less than about 0.05% by weight short chain triglycerides (SCT); wherein the fat and protein comprises a ratio of 0.05:1 to 1:1 by weight medium chain triglycerides (MCT) to protein.

* * * * *